(12) United States Patent
Sanderson et al.

(10) Patent No.: US 6,391,130 B1
(45) Date of Patent: May 21, 2002

(54) PROCESS FOR MAKING 2,4,6,8,10,12-HEXANITRO-2,4,6,8,10,12-HEXAAZATETRACYCLO[5.5.0.0^{5,9}0^{3,11}]-DODECANE

(75) Inventors: Andrew J. Sanderson, North Ogden; Kirstin Warner, Ogden; Robert B. Wardle, Logan, all of UT (US)

(73) Assignee: Alliant Techsystems Inc., Edina, MN (US)

(*) Notice: Subject to any disclaimer, the term of this patent is extended or adjusted under 35 U.S.C. 154(b) by 0 days.

(21) Appl. No.: 09/503,726

(22) Filed: Feb. 15, 2000

Related U.S. Application Data

(60) Provisional application No. 60/120,187, filed on Feb. 16, 1999.

(51) Int. Cl.[7] .................. C07D 295/28; C06B 25/34
(52) U.S. Cl. ........................................ 149/92; 540/554
(58) Field of Search ......................... 540/554; 149/92

(56) References Cited

U.S. PATENT DOCUMENTS

| | | | |
|---|---|---|---|
| 5,124,493 A | 6/1992 | Lukasavage et al. | 568/924 |
| 5,498,711 A | 3/1996 | Highsmith et al. | 540/546 |
| 5,693,794 A | 12/1997 | Nielsen | 540/554 |
| 5,723,604 A | 3/1998 | Cannizzo et al. | 540/556 |
| 5,739,325 A | 4/1998 | Wardle et al. | 540/554 |
| 5,874,574 A | 2/1999 | Johnston et al. | 540/475 |
| 6,147,209 A | 11/2000 | Wardle et al. | 540/556 |

FOREIGN PATENT DOCUMENTS

| | | |
|---|---|---|
| EP | 0753 519 A1 | 1/1997 |
| EP | 0 919 556 A1 | 6/1999 |
| JP | WO 98/05666 | 2/1998 |

OTHER PUBLICATIONS

Technical Report, Scale–Up of CL–20 Synthesis and Characterization of the Resulting Product, Nov. 18–19, 1997, JANNAF Workshop, Ogden, Utah.

Bellamy, "Reductive Debenzylation of Hexabenzylhexaazaisowurtzitane," Pergamon, Tetrahedron vol. 51. No. 6, pp. 4711–4722, 1995.

*Primary Examiner*—Mukund J. Shah
*Assistant Examiner*—Thomas McKejie

(57) ABSTRACT

In this process 2,6,8,12-tetraacetyl-2,4,6,8,10,12-hexaazatetracyclo-[5.5.0.0^{5,9}0^{3,11}]-dodecane ("TADH") is subjected to nitrolysis in the presence of a mixed acid to form HNIW. The mixed acid comprises at least one nitronium ion source (preferably nitric acid) and at least one strong acid (preferably sulfuric acid) capable of generating a nitronium ion from the source. The ratio of nitronium ion source to strong acid and the amount of TADH used are selected so that, in the event that the nitrolysis reaction is carried out at 85° C., 99% nitramine conversion will occur within ten minutes.

15 Claims, 1 Drawing Sheet

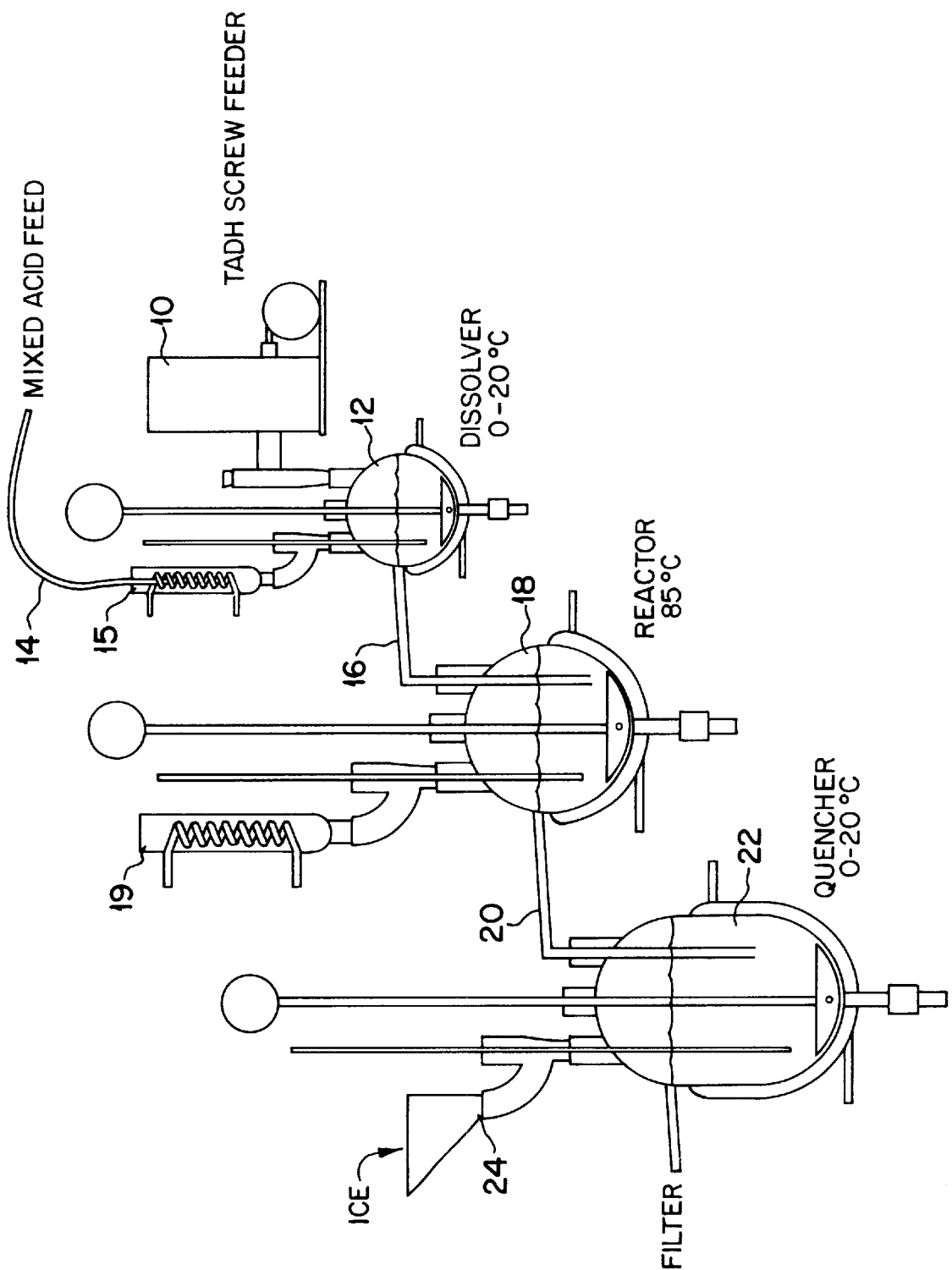

PROCESS FOR MAKING 2,4,6,8,10,12-HEXANITRO-2,4,6,8,10,12-HEXAAZATETRACYCLO[5.5.0.0$^{5,9}$0$^{3,11}$]-DODECANE

RELATED APPLICATIONS

This application claims the benefit of priority of provisional application No. 60/120,187 filed in the U.S. Patent & Trademark Office on Feb. 16, 1999, the complete disclosure of which is incorporated herein by reference.

BACKGROUND OF THE INVENTION

1. Field of the Invention

This invention relates to a process for making 2,4,6,8,10,12-hexanitro-2,4,6,8,10,12-hexaazatetracyclo[5.5.0.0.$^{5,9}$.0$^{3,11}$]-dodecane, also commonly known as 2,4,6,8,10,12-hexanitro-2,4,6,8,10,12-hexaazaisowurtzitane, HNIW or CL-20, and in particular relates to a continuous process for making HNIW.

2. Description of the Related Art

HNIW is a polycyclic caged nitramine oxidizer having the following chemical structure:

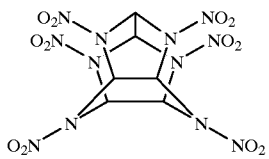

For most existing weapons systems, the most critical ingredient in terms of propellant and explosive performance is the oxidizer. HNIW, with its substantial increase in performance output, presents significant opportunities in energy capabilities for propellant and explosive systems. It may be possible to replace existing weapons system energetic fillers with HNIW to increase shaped charge anti-armor penetration, increase missile payload velocity and standoff, increase underwater torpedo effectiveness and lethality, and improve gun propellant impetus.

In view of the potential plethora of applications for HNIW, it would be advantageous to develop a continuous process for making HNIW in high production capacities.

According to one known process for making HNIW, HNIW is synthesized via nitration of the precursor, tetraacetyldiformyl-hexaazaisowurtzitane ("TADF"), as shown below:

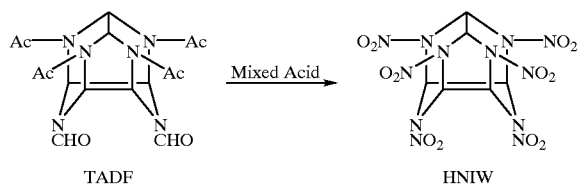

TADF can be synthesized according to the procedure described in U.S. Pat. No. 5,739,325 to Wardle, entitled "Hydrogenolysis of 2,4,6,8,10,12-hexabenzyl-2,4,6,8,10,12-hexaazatetracyclo[5.5.0.0 $^{5,9}$.0$^{3,11}$]dodecane," the complete disclosure of which is incorporated herein by reference. However, nitrolysis of TADF to form HNIW of acceptable purity has been found to require long reaction times, such as on the order of 2 to 3 hours. Attempts to increase the kinetics of the reaction and shorten reaction times have resulted in the formation of formyl-containing impurities. Thus, it would be extremely difficult to produce HNIW of acceptable purity via a continuous process which involves the nitrolysis of TADF to HNIW, since long residence times are required for the nitrolysis of the presursor, TADF, to HNIW.

A series of acyl group-containing hexaazaisowurtzitane derivatives is disclosed in EP 0 753 519 A1, the complete disclosure of which is incorporated herein by reference. Examples 20 and 22 of this European publication collectively disclose a process in which 2,6,8,12-tetraacetyl-2,4,6,8,10,12-hexaazatetracyclo[5.5.0.0$^{5,9}$0$^{3,11}$]-dodecane (also known as tetraacetylhexaazaisowurtzitane or "TADH") is, in a stepwise manner, first nitrosated with sodium nitrate and then oxidized with 100% nitric acid to form a dinitro intermediate, dinitrotetraacetylhexaazaisowurtzitane. After distilling off the nitric acid, the dinitro intermediate is reacted with a mixed acid consisting of 50 vol. % nitric acid (100%) and 50 vol. % sulfuric acid (100%) to form HNIW. However, it is reported that the second stage of the reaction took 8 hours at 0° C. followed by 67 hours at room temperature to go to completion.

It would therefore be a significant advancement in the art to provide a reasonably rapid, continuous process for the formation of HNIW. In particular, it would be a noteworthy advance in the synthesis of HNIW to significantly shorten the nitrolysis of TADF or TADH to HNIW.

SUMMARY OF THE INVENTION

In accordance with the principles of this invention, the above-mentioned and other advances in the art are attained by the provision of a process in which TADF is replaced with 2,6,8,12-tetraacetyl-2,4,6,8,10,12-hexaazatetracyclo-[5.5.0.0$^{5,9}$0$^{3,11}$]-dodecane ("TADH"), and subjecting the TADH to nitrolysis in the presence of a mixed acid to form HNIW. The mixed acid comprises at least one nitronium ion source and at least one strong acid preferably nitric acid and sulfuric acid, respectively) capable of generating nitronium ions from said source. The nitrolysis reaction is shown below:

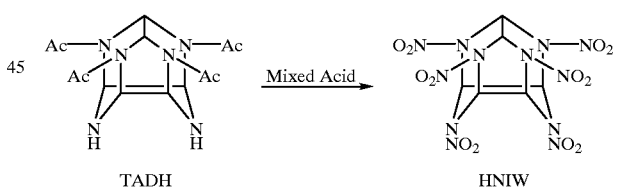

The volumetric ratio of nitronium ion source (e.g., HNO$_3$) to strong acid (e.g., H$_2$SO$_4$) is preferably selected so that when reacted at a temperature of 85° C., a product having undergone at least 99% conversion to nitramine is rapidly formed, preferably in no more than 10 minutes. More particularly, the volumetric ratio of HNO$_3$:H$_2$SO$_4$ is preferably about 7:3.

As referred to herein, the purity of the HNIW product can be rated based on a "conversion to nitramine" standard. Conversion to nitramine means 100 multiplied by the ratio of the number of available substituted and unsubstituted nitrogen groups (of the analyzed nitramines) converted to nitramine groups (N—NO$_2$) divided by the total number of substituted (N—R) and unsubstituted (N—H) nitrogen groups (of the analyzed nitramines) that are capable of being converted to nitramine groups. The conversion to nitramine is determined by NMR analysis as follows. Analysis of HNIW by NMR produces two peaks. The first of these peaks represents the protons at the 3, 5,9, and 11-positions of HNIW, whereas the second of these peaks represents the protons at the 1-position and 7-position of HNIW. Generally, the first peak is approximately twice the area of the second peak, since the first peak accounts for twice as many protons as the second peak. Other nitramine impurities produced during HNIW synthesis are present during NMR analysis and produce their own distinct peaks. Nitramine conversion is determined by taking the ratio of the area of the second HNIW peak (for the 1,7-positioned protons) to the greatest area of any peak produced by protons of a nitramine other than HNIW, i.e., a nitramine impurity. Thus, a conversion to nitramine of at least 99% HNIW means that the smaller HNIW peak area of the 1,7-position protons from NMR analysis is at least 99 times the area of the peak of greatest area produced by protons of a nitramine impurity (that is, a nitramine other than HNIW).

In accordance with a preferred embodiment of this invention, the process of converting TADH to HNIW by nitrolysis with the mixed acid is conducted in a continuous manner.

These and other objects, features, and advantages of the present invention will become apparent from the following detailed description of the invention when taken in conjunction with the accompanying Figure which illustrates, by way of example, the principles of this invention.

BRIEF DESCRIPTION OF THE FIGURE

The accompanying FIGURE is a schematic view of a flow diagram of a continuous process for the nitrolysis of TADH to HNIW in accordance with an embodiment of this invention.

DETAILED DESCRIPTION OF THE INVENTION

As mentioned above, Examples 20 and 22 of EP 0 753 519 A1 collectively disclose a process in which TADH is selected as a precursor and, after being nitrosated and thereafter nitrated, is reacted with a mixed acid consisting of 50 vol. % nitric acid (100%) and 50 vol. % sulfuric acid (100%). However, it is reported that the mixed acid took 67 hours at room temperature to drive the reaction to completion.

Intuitively, and as dictated by known chemistry principles, it would seem that the rate of reaction would be increased by increasing the sulfuric acid concentration of the mixed acid, since an increase in the sulfuric acid concentration generates a corresponding increase in nitronium ion activity. However, the present inventors discovered, to their surprise, that high concentrations of strong acids, such as sulfuric acid, decrease the rate of HNIW formation. High proportions of such strong acids result in impure HNIW containing acetyl substituents being quickly precipitated from the reaction mixture before completion of the nitrolysis of TADH to HNIW. Hence, subsequent nitrolysis of the precipitated, partly nitrated TADH is consequently slowed.

The present inventors found that the reaction rate for the nitrolysis of TADH to HNIW can advantageously be increased by nitrolysis of the TADH with a mixture comprising nitric acid and a strong acid, preferably sulfuric acid, at prescribed volumetric ratios. The optimum volumetric ratio of nitronium ion source to strong acid is dependent upon the nitronium ion source and strong acid selected, as well as the amount of TADH present, since the concentration of TADH affects the amount of water generated and, hence, solubility. Generally, however, a volumetric ratio of $HNO_3:H_2SO_4$ in a range of from about 6:4 to about 8:2 is preferred. At this preferred range, nitrolysis to 99% nitramine conversion can be achieved in less than 20 minutes at 85° C. (A temperature of 85° C. is presented for illustrative purposes only as a control temperature at which nitramine conversion is measured as a function of time, although 85° C. is particularly suitable since it drives the kinetics of the reaction without causing the acids to boil. It is to be understood that this process may be carried out at other temperatures, but preferably is carried out to have ratios of mixed acid components and ingredients selected so that, if the treatment step had been carried out at 85° C., a 99% conversion to nitramine would be obtained in not more than 10 minutes.) Most preferably, the volumetric ratio of $HNO_3:H_2SO_4$ is about 7:3, so that the reaction is capable of proceeding at 85° C. to form a product of 99% conversion to nitramine (NMR) in not more than 10 minutes. Another strong acid that can be used in lieu of sulfuric acid is methylsulfonic acid $CH_3SO_2OH$, although methylsulfonic acid should be used in a volumetric ratio closer to about 7:3 to provide the nitrolysis reaction with the capability of forming 99% conversion to nitramine at 85° C. within 20 minutes.

The ratio of mixed acid (in milliliters) to TADH (in grams) is preferably at least about 7:1, can be in a range of from about 7:1 to about 30:1, more preferably is about 7.5:1 to about 10:1, and most preferably is about 8:1. At ratios less than about 7:1, the efficiency of the conversion to nitramine is adversely effected. Ratios greater than about 30:1 are discouraged for efficiency and economic reasons.

The acid mixture may contain up to about 5% by volume of water, but most preferably is substantially free of water, meaning that it has less than 2% by volume of water. More preferably, the acid mixture has less than 1% by volume of water.

The FIGURE depicts an exemplary continuous flow process for converting TADH to HNIW. In the illustrated process, TADH is fed through a screw feeder 10 into a first cooling vessel 12, which is preferably operated at about 0–20° C. Also fed into the first cooling vessel 12 through conduit 14 containing a condenser 15 is a mixed acid, which is introduced in the prescribed concentrations to dissolve the TADH in about 2–3 minutes. The mixed acid preferably comprises a mixture of sulfuric acid and nitric acid, added in such amounts that the volumetric ratio of $HNO_3:H_2SO_4$ is preferably about 7:3. A portion of the solution is continuously tapped off from the first cooling vessel 12 and fed through conduit 16 into a reactor 18, which contains condenser 19 and is operated at a temperature of about 85° C. The solution is maintained in the reactor 18 for a residence time of 10 minutes to form HNIW, which is removed through conduit 20 and fed into a second cooling vessel 22. Ice is fed through feeder 24 into the second cooling vessel 22 to maintain the second cooling vessel 22 at an operating temperature of about 0–20° C. The volumetric rate of the ice fed through feeder 24 is preferably equal to the volumetric rate of acid feed to the second cooling vessel 22. A product stream overflowing from the vessel 22 is filtered and collected.

TADH is available through Asahi of Osaka, Japan. As an alternative source of TADH, a process for preparing TADH will now be explained in detail. It is understood, however, that the invention is not to be restricted to this process embodiment.

TADH can be prepared from hexabenzylhexaazaisowurtzitane (HBIW) as a precursor. HBIW can be synthesized according to the procedure described by Nielsen et al. in "Polyazapolycyclics by Condensation of Aldehydes with Amines. 2. Formation of 2,4,6,8,10,12-Hexabenzyl-2,4,6,8, 10,12-hexaazatetracyclo[5.5.0.0$^{5,9}$.0$^{3,11}$]dodecanes from Glyoxal and Benzylamines," Journal of Organic Chemistry, Vol. 55, pp. 1459–66 (1990) and U.S. Pat. No. 5,723,604, the complete disclosures of which are incorporated herein by reference. It is understood, however, that equivalents of HBIW might also be used, such as precursor compounds containing substitutions for one or more of the benzyl groups.

HBIW is subjected to a hydrogenolysis step to form tetraacetyldibenzylhexaazaisowurtzitane ("TADB"), as described in U.S. Pat. No. 5,739,325 and as shown below:

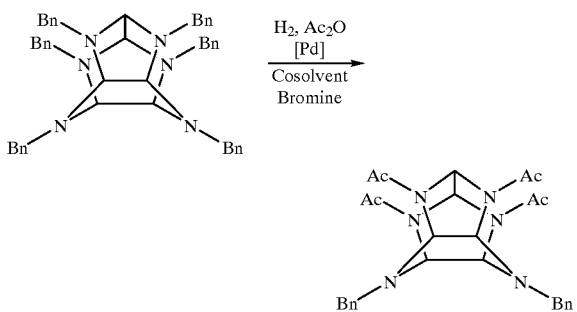

In this preparatory process, a quantity of HBIW, a cosolvent, and a bromine source are placed into a reaction vessel. Representative of suitable cosolvents are N,N-dimethylformamide ("DMF"), N-methylpyrollidone ("NMP"), and 1,2-dimethoxyethane. Suitable bromine sources include molecules having active bromine, such as benzyl bromide, acetyl bromide, and bromine gas ($Br_2$). The HBIW, cosolvent, and bromine source are preferably mixed in an atmosphere which is substantially non-reactive with hydrogen. For instance, the reaction vessel can be purged with an inert atmosphere, such as nitrogen. Alternatively, the reaction vessel atmosphere can be removed by vacuum. Acetic anhydride and a palladium hydrogenolysis catalyst are added to the reaction vessel, followed immediately by introduction of hydrogen into the reaction vessel.

The hydrogenolysis catalyst is preferably added to the reaction vessel in an amount less than 10% by weight based on the HBIW substrate. Typical hydrogenolysis catalysts which can be used include $Pd(OH)_2$, Pd, and mixtures thereof on carbon commonly used as a catalyst support. Several standard palladium metal and Pearlman's-type catalysts have both been found to be suitable. Such catalysts are commercially available. Similarly, catalysts that are provided either water-wet or dry have been useful. The weight percent of active palladium on carbon is preferably less than 10%, more preferably less than 5%, and can be as low as 3%.

The hydrogenolysis catalyst is preferably substantially free of water. This can be accomplished by washing the catalyst with the co-solvent prior to introduction into the reaction vessel to remove water associated with the catalyst. The palladium catalyst is normally shipped water-wet, with approximately 50% of the weight being water. While not wishing to be bound by theory, it is presently believed that acetic acid, formed by reaction of acetic anhydride in the reaction mixture with the water on the catalyst, reduces the yield and increases the chances of a failed or incomplete reaction. Previous efforts at water removal, such as vacuum drying, which was unacceptable due to fire hazard and catalyst activity reduction, or washing with acetic anhydride, did not fully remove water and left acetic acid present. Washing with the polar co-solvent effectively removes water and does not introduce deleterious side products or reduce catalyst activity.

It has been discovered that addition of the reactive acetic anhydride immediately prior to hydrogen introduction improves the reaction yield, rate, and reproducibility. The acetic anhydride is added immediately prior to hydrogen introduction so that the acetic anhydride does not have time to react with the HBIW to form N-benzylacetamide which acts as a catalyst poison, which is a major contributor to incomplete or low yield reactions. N-benzylacetamide is formed by the acid catalyzed decomposition of HBIW to yield "free" benzyl amine followed by acetylation of the benzyl amine by acetic anhydride. This reaction occurs slowly once the reaction mixture is together. To minimize this unwanted reaction, the co-solvent and HBIW are preferably placed in the reaction vessel first, followed by the bromine source. The contents are thoroughly mixed and placed under a nitrogen atmosphere. The acetic anhydride and the washed palladium catalyst are then added quickly, followed immediately by hydrogen introduction. Once the acetic anhydride is added to the HBIW, the hydrogen should be added rapidly to inhibit unwanted side reactions.

Once hydrogen is introduced into the reaction vessel, the HBIW is converted to TADB, which precipitates onto the palladium hydrogenolysis catalyst and is easily recovered by filtration. The co-solvent assists in providing complete precipitation. After the hydrogenolysis is complete, the product and catalyst are filtered from the liquid phase and washed with a solvent, such as denatured ethanol, methanol, or isopropanol. The solvent is preferably miscible with the DMF, acetic anhydride, and acetic acid so that these compounds can later be removed from the TADB product. The solvent is also preferably immiscible with the desired TADB product so that the TADB is not dissolved and washed away with the solvent. It is also important that the solvent have not effect on the subsequently hydrogenolysis reaction.

The filtered and washed TADB is sufficiently pure for a second hydrogenolysis reaction in which the TADB product and catalyst are reacted to form TADH, as depicted as follows:

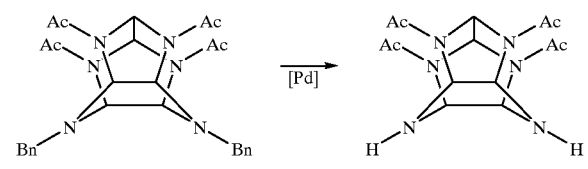

A suitable catalyst and solvent for the second hydrogenolysis reaction are $Pd(OAc)_2$ and acetic acid, respectively. The second hydrogenolysis reaction is slower than the first hydrogenolysis reaction, due to the reduced activity of the last two benzyl groups of the TADB towards hydrogenation. This second hydrogenolysis step is preferably performed in the absence of formic acid or other acid to prevent the formation of TADF or equivalent compounds.

The catalyst is removed by filtration, and the product is recovered by evaporation of the volatile solvents. The catalyst may be recycled and used again in the process or it may be reprocessed by the catalyst manufacturer. The TADH product thus obtained is of a purity suitable for direct use in the nitration reaction to produce HNIW.

The HNIW can be thereafter crystallized to ε-polymorph HNIW in accordance with the technique disclosed in allowed U.S. Pat. No. 5,874,574 the complete disclosures of which are incorporated herein by reference. (According to this U.S. patent, a quantity of CL-20 is dissolved in a solution containing a CL-20 solvent, such as ethyl acetate, and water. The resulting mixture consists of two liquid phases: an aqueous phase and a wet solvent phase. The pH of the aqueous phase can be tested and adjusted at this point as desired. The CL-20 is dissolved in the wet solvent phase, which is dried by removing a solvent/water azeotrope according to conventional distillation techniques, thereby forming a dry solvent phase containing the CL-20. A low density non-polar CL-20 non-solvent, such as hexane, cyclohexane, heptane, octane, benzene, toluene, xylene, mineral oil, petroleum ethers, and ligroin, is added to the dry CL-20 solvent phase to cause crystallization of ϵ-polymorph CL-20. The low density non-polar non-solvent preferably has a density less than water. The CL-20 crystals are then separated from the non-solvent and the solvent by adding sufficient water to displace the non-solvent and the solvent from the surface of the ϵCL-20 crystals. In this fashion, ϵ-polymorph CL-20 is made wet for later handling, packaging, and shipping. The ratio of water to CL-20 should typically range from 1:7 to 3:1, by volume. More water can be easily used in the system, but larger quantities of water will require larger equipment for separating and recycling the water. The wet CL-20 is collected and the CL-20 non-solvent, CL-20 solvent, and excess water are removed to separate and recycle the individual solvents.)

The conversion to nitramine as reported and claimed herein is determined by NMR standards by the procedure detailed above in the Summary and the Example below. However, it is to be understood that other standards for determining nitramine conversion exist, although such other standards may alter the appropriate timing for obtaining 99% conversion and, therefore, should not be used in determining the literal and equivalent scope of the appended claims. One alternative, unclassified standard for determining HNIW purity was developed pursuant to a Standardization Agreement between the North Atlantic Treaty Organization (NATO) and the Military Agency for Standardization (MAS). This standard is STANAG4566. Under this Standardization Agreement, chemical purity is determined by using high performance liquid chromatograph (HPLC) equipped with a 226 nm UV detector and an integrator or computer link up to a data acquisition. Generally, a conversion of 97% (as measured by the STANAG4566) can be achieved in less than 30 minutes, preferably in less than 20 minutes.

The unexpected superior results obtained by practicing the present invention are manifested by the following experiments, which are presented for the purpose of explanation and are not to be considered limiting on the scope of the invention.

EXAMPLES

Examples 1–5

1 gram of TADH substrate was cooled with an ice bath to 6° C. A mixed acid solution of $H_2SO_4$/$HNO_3$ (in the concentrations specified in the Table below) at 25° C. was added to the ice bath. The mixture was then heated in a bath having a temperature of 95° C., and samples were removed and tested for nitramine conversion in 5 minute intervals as specified in the Table. The results are reported in the Table below.

TABLE

| | $H_2SO_4$ (ml) | $HNO_3$ (ml) | Time (min) | Conversion to Nitramine |
|---|---|---|---|---|
| Example 1 | 1 | 9 | 20 | 72 |
| | 1 | 9 | 25 | 91 |
| | 1 | 9 | 30 | 91 |
| | 1 | 9 | 35 | 97 |
| | 1 | 9 | 40 | 98 |
| Example 2 | 2 | 8 | 15 | 92 |
| | 2 | 8 | 20 | 100 |
| | 2 | 8 | 25 | 100 |
| | 2 | 8 | 30 | 100 |
| | 2 | 8 | 35 | 100 |
| | 2 | 8 | 40 | 100 |
| Example 3 | 3 | 7 | 10 | 100 |
| | 3 | 7 | 15 | 100 |
| | 3 | 7 | 20 | 100 |
| | 3 | 7 | 25 | 100 |
| | 3 | 7 | 30 | 100 |
| | 3 | 7 | 35 | 100 |
| | 3 | 7 | 40 | 100 |
| Example 4 | 4 | 6 | 5 | 91 |
| | 4 | 6 | 10 | 91 |
| | 4 | 6 | 15 | 88 |
| | 4 | 6 | 20 | 100 |
| | 4 | 6 | 25 | 100 |
| | 4 | 6 | 30 | 100 |
| | 4 | 6 | 35 | 100 |
| | 4 | 6 | 40 | 100 |
| Example 5 | 5 | 5 | 10 | 71 |
| | 5 | 5 | 15 | 89 |
| | 5 | 5 | 20 | 92 |
| | 5 | 5 | 30 | 98 |

Analysis of the samples for conversion to nitramine was generally performed in accordance with the following procedures. A small amount (ca. 80 mg was dissolved in D6-acetone and was recorded 1 H spectrum on a 300 MHz Varian XL300 nmr spectrometer. HNIW has two peaks at about 8.23 and 8.36 ppm, with an integral ratio of 1:2. The extent of reaction or conversion was assessed by taking the ratio of the peak areas of the smaller HNIW peak to the largest of any impurity peak observed between 7 and 9 ppm.

As shown from these results, a mixed acid ratio of $HNO_3$:$H_2SO_4$ of 7:3 produced a product having approximately nitramine conversion within 10 minutes. By contrast, a mixed acid ratio of $HNO_3$:$H_2SO_4$ of 9:1 did not produce a product having a 99% nitramine conversion within the 40 minutes of testing. A mixed acid ration of 5:5 did not produce a product having 99% nitramine conversion within 30 minutes of testing. Mixed acid ratios of $HNO_3$:$H_2SO_4$ of 8:2 and 6:4 each took about 20 minutes to undergo 99% nitramine conversion.

Example 6

Preparation of HBIW

To a mixture of 12 kg of DMF and 70 kg (686 moles) of acetic anhydride in a 75 gallon stirred autoclave (steel reactor) were added 43.2 kg (61 moles) of HBIW, 0.781 (7.4 moles) of bromobenzene, and 4.63 kg of a 55.3% moisture 10% palladium on carbon catalyst (dry weight of catalyst was 2.07 kg). The vessel was purged four times with hydrogen. During the purges, the temperature of the reactor rose from 21.3° C. to 25.2°C. The reaction was then stirred under 50 psi pressure of hydrogen introduced into the reaction mixture via a sparge ring. Over the next 30 minutes, the reaction temperature rose to 51.4° C. and cold water was then circulated through the jacket of the flask to control the exotherm. Approximately 140 moles of hydrogen (based on pressure drop in the hydrogen tank) were consumed during this period not counting any hydrogen consumed during the purges. Over the next 1.5 hours, another 120 moles of hydrogen were consumed with the reaction temperature then at 43.1° C. (cold water was stopped circulating when the reaction temperature dropped below 35° C.). The reaction was allowed to stir an additional 21 hours during which time another 40 moles of hydrogen were consumed (total of 300 moles versus a theoretical 250 moles for the reaction). The reactor was purged three times with nitrogen then the reaction mixture was filtered. The solids were washed with roughly 130 liters of denatured ethanol to afford the desired product along with palladium catalyst slightly moist with ethanol and trace amounts of DMF as a gray solid. In a total of three reactions ran as described above, a total of 85.7 kg (82–85% yield) of the product mixture were obtained.

Example 7

Preparation of TADH

In a Parr apparatus was placed 6 g of HBIW, 200 ml acetic anhydride, 1.5 g Pearlman's palladium hydroxide on charcoal (20% Pd) and 0.17 g bromobenzene. After flushing the apparatus with hydrogen, the pressure of hydrogen was increased to 50 psi for 18 hours. After this time the catalysts/product mixture was removed by filtration, and extracted with twice with 80 ml boiling chloroform. The extract was concentrated and triturated with acetonitrile to give TADB. 3.67 g of this TADB, 1.6 g Pd(OAc)$_2$, and 150 ml acetic acid were placed in a Parr apparatus. After flushing the apparatus with hydrogen, the pressure of hydrogen was increased to 3.455 kgf/cm$^2$ for 15 hours. After this time, the reaction mixture was filtered and the mother liquor evaporated to give a solid which was washed with 100 ml ethyl acetate to yield 1.67 g of TADH.

The foregoing detailed description of the preferred embodiments of the invention has been provided for the purpose of explaining the principles of the invention and its practical application, thereby enabling others skilled in the art to understand the invention for various embodiments and with various modifications as are suited to the particular use contemplated. This description is not intended to be exhaustive or to limit the invention to the precise embodiments disclosed. Modifications and equivalents will be apparent to practitioners skilled in this art and are encompassed within the spirit and scope of the appended claims.

We claim:

1. A process for the nitrolysis of 2,6,8,12-tetraacetyl-2,4,6,8,10,12-hexaazatetracyclo-[5.5.0.0$^{5,9}$0$^{3,11}$]-dodecane ("TADH") to form 2,4,6,8,10,12-hexanitro-2,4,6,8,10,12-hexaazatetracyclo-[5.5.0.0$^{5,9}$0$^{3,11}$]-dodecane ("HNIW"), said process comprising treating said TADH with a mixed acid comprising HNO$_3$ and H$_2$SO$_4$ at about 85° C. to form HNIW at a rate of at least 99 percent conversion to nitramine in no more than 10 minutes, wherein a volumetric ratio of HNO$_3$ and H$_2$SO$_4$ is in a range of from about 6:4 to about 8:2.

2. A process according to claim 1, wherein said volumetric ratio is about 7:3.

3. A process according to claim 1, wherein said process is conducted at 85° C.

4. A process according to claim 1, wherein a ratio of said TADH in grams to said mixed acid in milliliters is in a range of from about 1:7 to about 1:30.

5. A process according to claim 1, wherein a ratio of said TADH in grams to said mixed acid in milliliters is in a range of from about 1:7.5 to about 1:10.

6. A process according to claim 1, wherein a ratio of said TADH in grams to said mixed acid in milliliters is about 1:8.

7. A process according to claim 1, wherein said process is continuous.

8. A process for the nitrolysis of 2,6,8,12-tetraacetyl-2,4,6,8,10,12-hexaazatetracyclo-[5.5.0.0$^{5,9}$0$^{3,11}$]-dodecane ("TADH") to form 2,4,6,8,10,12-hexanitro-2,4,6,8,10,12-hexaaazatetracyclo-[5.5.0.0$^{5,9}$0$^{3,11}$]-dodecane ("HNIW"), said process comprising:

introducing said TADH and a mixed acid into a first cooling vessel to dissolve said TADH and form a solution, said mixed acid comprising HNO$_3$ and H$_2$SO$_4$, wherein a volumetric ratio of HNO$_3$ to H$_2$SO$_4$ is in a range of from about 6:4 to about 8:2;

transferring said solution to a heated reaction vessel for reaction of said TADH with said mixed acid at about 85° C. to form HNIW at a rate of at least 99 percent conversion to nitramine in no more than 10 minutes; and transferring said solution to a second cooling vessel to cool said HNIW.

9. A process according to claim 8, wherein said volumetric ratio is about 7:3.

10. A process according to claim 8, wherein said first and second cooling vessels are operated in a range of from about 0° C. to about 20° C.

11. A process according to claim 8, wherein said heated reaction vessel is operated at 85° C.

12. A process according to claim 8, wherein a ratio of said TADH in grams to said mixed acid in milliliters is in a range of from about 1:7 to about 1:30.

13. A process according to claim 8, wherein a ratio of said TADH in grams to said mixed acid in milliliters is in a range of from about 1:7.5 to about 1:10.

14. A process according to claim 8, wherein a ratio of said TADH in grams to said mixed acid in milliliters is about 1:8.

15. A process according to claim 8, wherein said process is continuous.

* * * * *